US012279957B2

United States Patent
Anusionwu

(10) Patent No.: US 12,279,957 B2
(45) Date of Patent: Apr. 22, 2025

(54) AUTOMATIC INFLATABLE PENILE PROSTHESIS DEVICE

(71) Applicant: Ifeanyichukwu Anusionwu, Sunnyvale, TX (US)

(72) Inventor: Ifeanyichukwu Anusionwu, Sunnyvale, TX (US)

( * ) Notice: Subject to any disclaimer, the term of this patent is extended or adjusted under 35 U.S.C. 154(b) by 0 days.

(21) Appl. No.: 18/825,938

(22) Filed: Sep. 5, 2024

(65) Prior Publication Data

US 2025/0073035 A1    Mar. 6, 2025

Related U.S. Application Data

(60) Provisional application No. 63/580,532, filed on Sep. 5, 2023.

(51) Int. Cl.
*A61F 2/26* (2006.01)
*A61F 2/48* (2006.01)

(52) U.S. Cl.
CPC ............... *A61F 2/26* (2013.01); *A61F 2/484* (2021.08)

(58) Field of Classification Search
CPC .................................. A61F 2/26; A61F 2/484
See application file for complete search history.

(56) References Cited

U.S. PATENT DOCUMENTS

| | | |
|---|---|---|
| 4,566,446 A | 1/1986 | Fogarty |
| 9,248,019 B2 | 2/2016 | Vaingast et al. |
| 2011/0015738 A1* | 1/2011 | Vaingast .................. A61F 2/004 623/14.13 |
| 2015/0320559 A1 | 11/2015 | Little |
| 2016/0220373 A1* | 8/2016 | Oben ......................... A61F 2/26 |
| 2019/0000626 A1 | 1/2019 | Tal et al. |
| 2020/0129295 A1* | 4/2020 | Kansas .............. A61B 17/8085 |

(Continued)

FOREIGN PATENT DOCUMENTS

WO    2015093681 A1    6/2015

OTHER PUBLICATIONS

Infla10® Pulse™ Series, retrieved from the internet, retrieved on Sep. 5, 2024; <URL: https://www.rigicon.com/inflatable-penile-prosthesis/>.

(Continued)

*Primary Examiner* — Carrie R Dorna
*Assistant Examiner* — Joshua Daryl D Lannu

(57) ABSTRACT

An automated penile prosthesis device is an inflatable prosthesis device that may be implanted through surgery. The device includes a penile prosthesis structure composed of an inflatable layer encapsulating a semi rigid structure. The device may include a pneumatic hose in fluid communication with the penile prosthesis and a fluid reservoir that includes an opening leading into an interior space of the fluid reservoir. Further, the device may include a pump configured for transferring the fluid from the fluid reservoir to the penile prosthesis structure through the pneumatic hose for transitioning the penile prosthesis from a flaccid state to an erected state. Furthermore, the pump may be configured for transferring the fluid for transitioning the penile prosthesis from the erected state to the flaccid state. Additionally, the device allows users to remotely control the pump through a remote controller. Thus, the device is a hybrid and automated penile prosthesis device.

19 Claims, 5 Drawing Sheets

(56) References Cited

U.S. PATENT DOCUMENTS

2021/0236288 A1    8/2021  Hamlin et al.
2022/0175531 A1*   6/2022  Grayson .................... A61F 2/26
2023/0133855 A1    5/2023  Marconi Toro et al.

OTHER PUBLICATIONS

AMS 700™, retrieved from the internet, retrieved on Sep. 5, 2024; <URL: https://www.bostonscientific.com/en-US/products/penile-prosthesis/ams-700-inflatable-penile-prosthesis.html>.
Tactra ™, retrieved from the internet, retrieved on Sep. 5, 2024; <URL: https://www.bostonscientific.com/en-US/products/penile-prosthesis/tactra--malleable-penile-prosthesis.html>.

* cited by examiner

AUTOMATIC INFLATABLE PENILE PROSTHESIS DEVICE

FIELD OF THE INVENTION

The present invention relates generally to the field of surgery. More specifically, the present invention is an automated prosthesis device for facilitating automatic inflatable penile implanting.

BACKGROUND OF THE INVENTION

The field of surgery is technologically important to several industries, business organizations, and/or individuals. In particular, the use of surgery is prevalent for methods, systems, and devices for facilitating automatic inflatable penile implanting. Erectile dysfunction affects over 18 million men in the United States of America, which is about 18.4% of the male population over the age of 20. There are various treatment options for erectile dysfunction including oral medication, injectable medications, vacuum erectile aid, and penile prosthesis. Existing techniques for treating erectile dysfunction are deficient with regard to several aspects. The currently available penile prosthesis models are either malleable or require manual inflation by the man to transition from a flaccid to an erect state. The malleable prosthesis neither provides a very firm nor very flaccid penis and therefore is less popular. The inflatable (two-piece or three-piece) penile prostheses have a cylinder that is placed in the penis, a pump that is placed in the scrotum, and in the case of a three-piece prosthesis, a reservoir that contains fluid for cycling the prosthesis. In the flaccid state, the fluid is maintained in the reservoir. When a user desires an erection, the user manually inflates the pump located in the scrotum. This process can be challenging for some users, especially if manual dexterity is limited, or the pump is placed or migrates to a part of the scrotum which is not easily accessible. Additionally, having so many pieces to the implant which are placed in so many different locations increase the morbidity of the surgery for placing the implant.

Therefore, there is a need for improved methods, systems, and devices for facilitating automatic inflatable penile implanting that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, a device for facilitating automatic inflatable penile implanting is disclosed. Accordingly, the device may include a penile prosthesis device composed of an inflatable expandable outer layer situated around a semirigid core layer. Preferably, the device may include a pneumatic hose in fluid communication with the penile prosthesis at a first end of the pneumatic hose. Further, the device may include a fluid reservoir that may include an opening leading into an interior space of the fluid reservoir. Further, the device may include a pump configured for transferring the fluid from the fluid reservoir to the penile prosthesis through the pneumatic hose for transitioning the penile prosthesis from a flaccid state to an erected state. Further, the pump may be configured for transferring the fluid from the penile prosthesis to the fluid reservoir through the pneumatic hose for transitioning the penile prosthesis from the erected state to the flaccid state. Further, the device may include a pump-controlling system configured for allowing a user to remotely control the pump. Further, the device may include a battery configured for supplying power to the device.

DETAILED DESCRIPTION OF THE INVENTION

Figure 1:
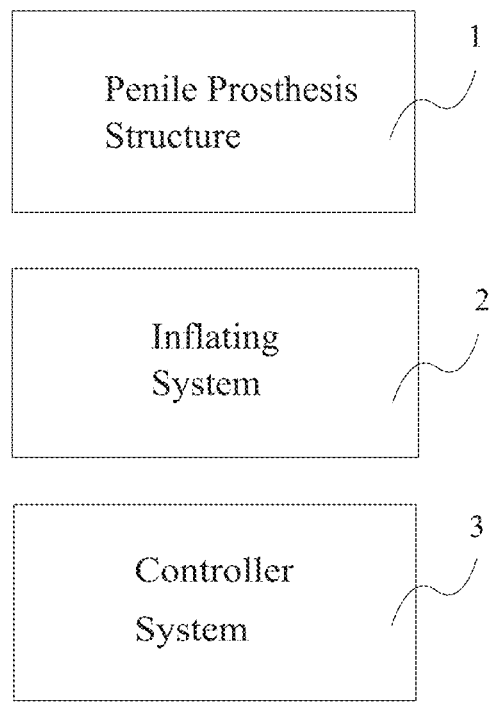
FIG. 1 is an overall block diagram of the present invention.
Figure 2:
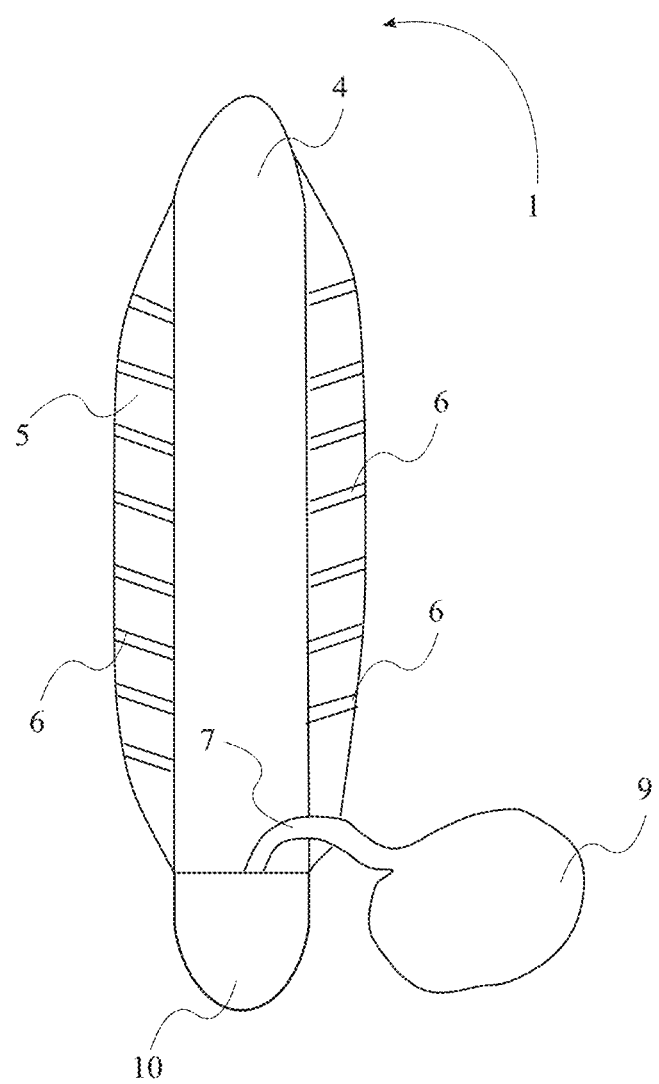
FIG. 2 is an illustration of a front cross sectional view of the present invention.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

In reference to FIG. 1 through FIG. 5, the present invention provides an automated and inflatable penile prosthesis device. The following description is in reference to FIG. 1 through FIG. 5.

According to a preferred embodiment, the present invention comprises a penile prosthesis structure 1, an inflating system 2, and a controller system 3. The controller system 3 helps control the functions and shape of the penile prosthesis structure 1 through the inflating system 2. More specifically, the present invention helps to transition the state of the penile prosthesis structure 1 according to the user's preference in a remotely controlled fashion. To accomplish this, the penile prosthesis structure 1 comprises a semirigid core 4, an inflatable layer 5. Preferably, the semirigid core 4 is made of silicone elastomers, which makes the semirigid core 4 malleable, yet rigid. The inflatable layer 5 is positioned around the semirigid core 4 in such a fashion that the inflatable layer 5 encapsulates the semirigid core 4 around the lateral walls. Preferably, the inflatable layer 5 is made of a bio flex material that may include an expandable structure made of thin polymer sheets that fold flat (to create the flaccid state) and can pop up into a rigid cylinder. Further, the plurality of veins 6 is small tubular structures. However, the semirigid core 4 and the inflatable layer 5 may comprise any other material, components, arrangement of components, etc. that are known to one of ordinary skill in the art, as long as the intents of the present invention are not altered. Furthermore, the present invention may comprise a plurality of veins 6, wherein the plurality of veins 6 is integrated within the inflatable layer 5 and the plurality of veins 6 is evenly distributed along a length of the inflatable layer 5. This is so that the plurality of veins 6 helps with transitioning the inflatable layer 5 into an inflated state and a deflated state uniformly.

In an alternate embodiment, the penile prosthesis structure 1 may not include the semirigid core 4 and may comprise only an automated inflatable layer 5.

In the preferred embodiment, the inflating system 2 is integrated between the controller system 3 and the penile prosthesis structure 1. This is because the inflating system 2 is configured to inflate the inflatable layer 5, according to the user's preference. To accomplish this, the controller system 3 is operatively coupled with the penile prosthesis structure 1 through the inflating system 2, wherein operating the controller system 3 governs transitioning of the penile prosthesis structure 1 between an erect state and a flaccid state. Thus, the present invention is an automated and hybrid penile prosthesis device that enables users to actuate erection according to their preferences.

A more detailed description of the present invention follows.

According to the preferred embodiment, the inflating system 2 comprises a pneumatic hose 7, a pump 8, and a fluid reservoir 9. Preferably, the fluid reservoir 9 is configured to hold a fluid, and the pneumatic hose 7 is connected between the pump 8 and the fluid reservoir 9 such that the pneumatic hose 7 is in fluid communication between the fluid reservoir 9, the pump 8, and the inflatable layer 5. This is so that the pneumatic hose 7 acts as a link between the inflatable layer 5 and the fluid reservoir 9. Further, the pump 8 is configured to pump the liquid back and forth between the inflatable layer 5 and the fluid reservoir 9. More specifically, the fluid is pumped into the plurality of veins 6. In other words, the pump 8 is operably coupled with the fluid reservoir 9, wherein operating the pump 8 transfers the fluid between the fluid reservoir 9 and the plurality of veins 6. It should be noted that, the pneumatic hose 7, the pump 8, and the fluid reservoir 9 may comprise any size, brand, technology, components, arrangement of components, etc. that are known to one of ordinary skill in the art, as long as the intents of the present invention are not altered. More specifically, the pump 8 is configured for transferring the fluid from the fluid reservoir 9 to the penile prosthesis structure 1 through the pneumatic hose 7, for the purpose of transitioning the penile prosthesis structure 1 from a flaccid state to an erect state. Similarly, the pump 8 may be configured for transferring the fluid from the penile prosthesis structure 1 to the fluid reservoir 9 through the pneumatic hose 7 for transitioning the penile prosthesis structure 1 from an erect state to a flaccid state. Thus, inflatable layer 5, or the plurality of veins 6 is filled with the fluid during the erect state, and the inflatable layer 5 or the plurality of veins 6 is empty of the fluid during the flaccid state.

According to the preferred embodiment, a pump-controlling system or the controller system 3 is configured for allowing a user to remotely control the pump. To that end, the controller system 3 comprises an electric and electronic system 10 and a remote-control device 11. Preferably, the electric and electronic system 10 is communicably coupled to the remote-control device 11, wherein the remote-control device is configured to remotely control functions of the electric and electronic system 10. Further, the electric and electronic system 10 and the inflating system 2 may be housed in the crus of the penis, which is the part of the penis attached to the pubic bone. In other words, the electric and electronic system 10 is connected adjacent to a terminal end of the penile prosthesis structure 1. Thus, the present invention enables limited components for implantation to decrease the morbidity of the penile prosthesis placement surgery.

Figure 3:
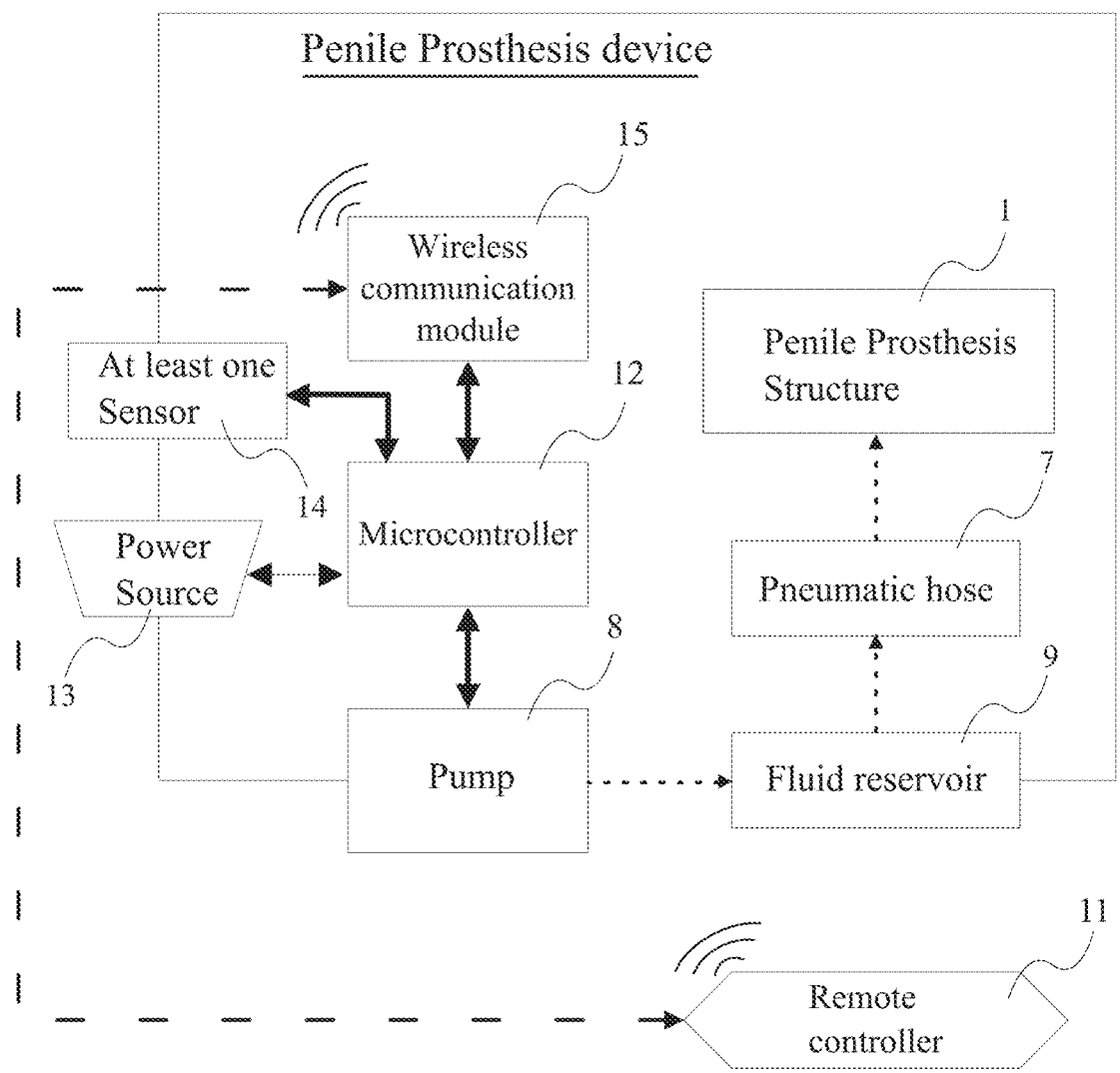
FIG. 3 is a system diagram of the present invention, wherein thinner lines represent electrically connected components, thicker lines represent electronically connected components, dotted lines represent fluidly connected components, and broken lines represent communicably connected components of the present invention.
Figure 4:
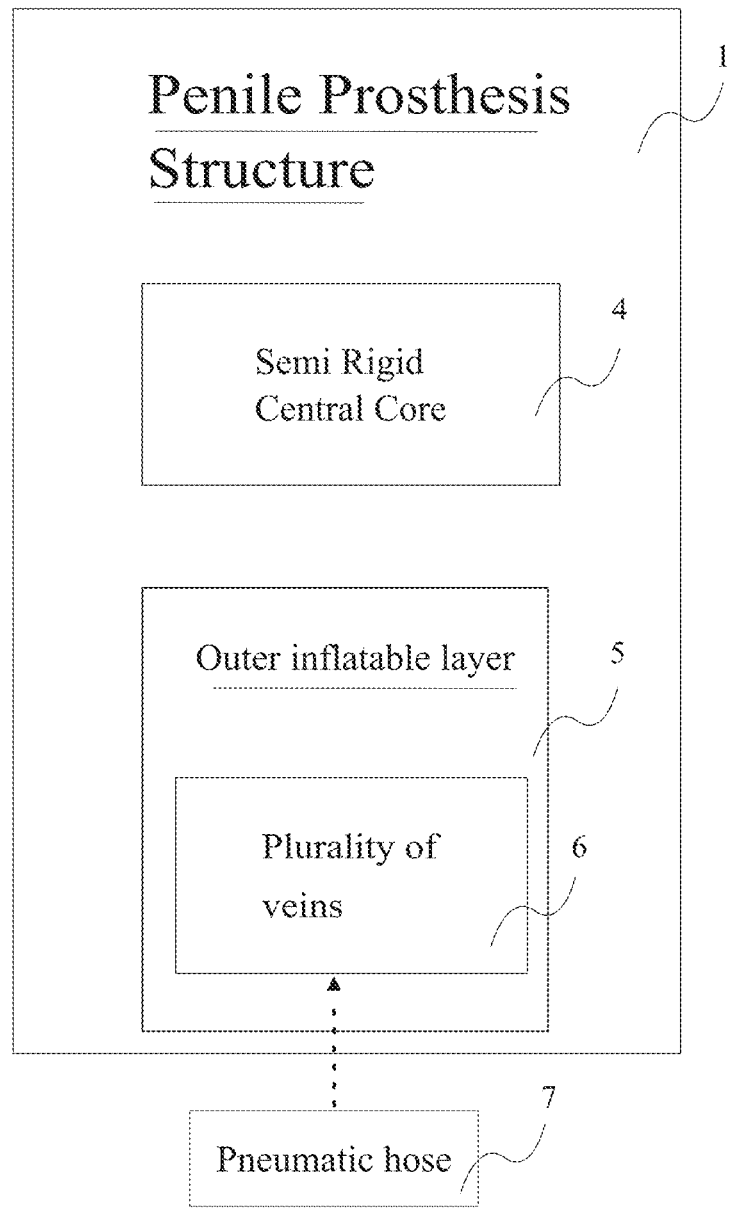
FIG. 4 is a block diagram of the penile prosthesis structure, wherein dotted lines represent fluid connection between components.
Figure 5:
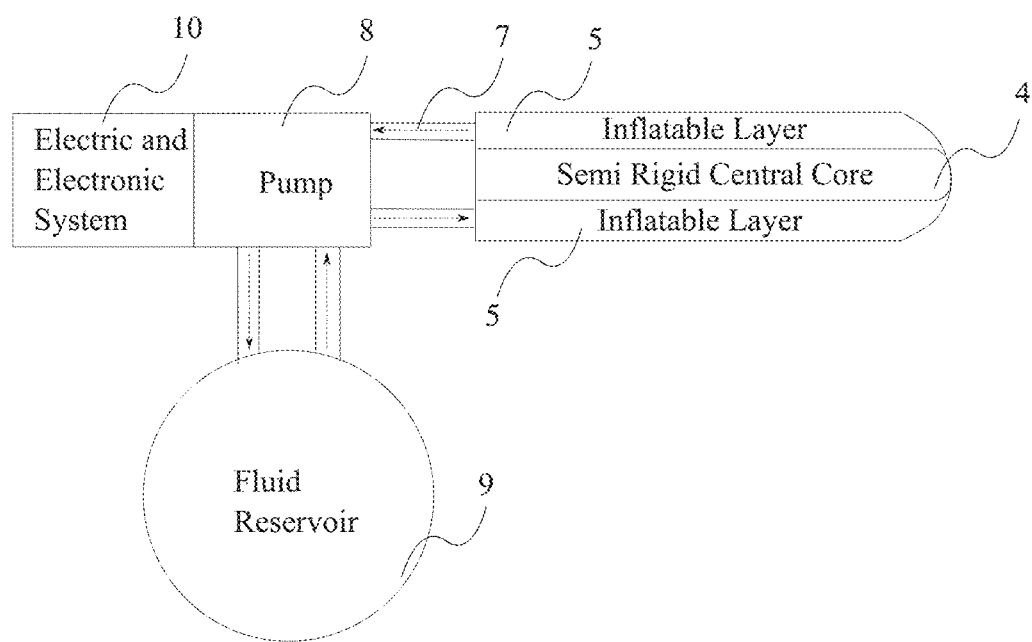
FIG. 5 is a system diagram of the side perspective view of the penile prosthesis device, according to the preferred embodiment of the present invention.

In reference to FIG. 3, the electric and electronic system 10 comprises a microcontroller 12, a power source 13, at least one sensor 14, and a wireless communication module 15. The microcontroller 12 is a processing device that controls the functions of all the components of the present invention. To that end, the microcontroller 12 is electronically connected to the inflating system 2, the at least one sensor 14, and the wireless communication module 15. The power source 13 provides electrical energy to the electrical components of the present invention. To that end, the power source is electrically connected to the microcontroller 12, the at least one sensor 14, and the pump 8. Preferably, the power source 13 is a 5 cc primary cell battery. The at least one sensor 14 may include, but may not be limited to, a length-measuring sensor for measuring at least one length of the penile prosthesis, a pressure-measuring sensor for measuring a pressure value in the penile prosthesis, etc. The wireless communication module 15 helps in communicating wirelessly with the remote-control device 11. In other words, the wireless communication module 15 is communicably connected to the remote-control device 11. Preferably, the remote-control device 11 is an application software, a keypad, or a button pad. However, the remote-control device 11 may comprise any other shape, size, technology, such as touch pad, voice activation, etc., that are known to one of ordinary skill in art, as long as the intents of the present invention are not altered. Thus, the user can control the operations of the penile prosthesis device remotely with the help of the remote-control device. Accordingly, the remote-control device 11 is detached from the penile prosthesis structure 1.

Thus, the automated inflatable penile prosthesis device includes limited components for implantation to decrease the morbidity of the penile prosthesis placement surgery. Further, the device may be appropriate for men with limited manual dexterity. Further, the device may be a fully automated penile prosthesis.

In summary, in the preferred embodiment, the device may include a penile prosthesis device composed of an inflatable layer 5 and a semirigid central core 4. Further, the device may include a fluid reservoir 9 that may include an opening leading into an interior space of the fluid reservoir 9. Further, the fluid reservoir 9 may be configured for storing a fluid. Further, the pneumatic hose 7 may be in fluid communication with the fluid reservoir 9. Further, the device may include a pump 8 configured for transferring the fluid from the fluid reservoir 9 to the penile prosthesis through the pneumatic hose 7, which thereby helps with transitioning the penile prosthesis structure 1 from a flaccid state to an erected state. Further, the pump 8 may be configured for transferring the fluid from the penile prosthesis structure 1 to the fluid reservoir 9 through the pneumatic hose 7 for transitioning the penile prosthesis structure 1 from the erected state to the flaccid state. Further, the device may include a pump-controlling system 3 configured for allowing a user to remotely control the pump 8. Further, the device may include a battery configured for supplying power to the device. Further, in some embodiments, the battery and the pneumatic hose 7 may be placeable in the crux of the penis of the user, wherein the battery may be suitable for clinical use.

Although the invention has been explained in relation to its preferred embodiment, it is to be understood that many other possible modifications and variations can be made without departing from the spirit and scope of the invention as hereinafter claimed.

What is claimed is:

1. An automated penile prosthesis device comprising:
a penile prosthesis structure;
an inflating system; and
a controller system;
the penile prosthesis structure comprising a semirigid core, an inflatable layer, and a plurality of veins;
the inflating system being integrated between the controller system and the penile prosthesis structure;
the inflatable layer encapsulating the semirigid core;
the plurality of veins being integrated within the inflatable layer;
the plurality of veins being evenly distributed along a length of the inflatable layer;
the inflating system being configured to inflate the inflatable layer; and
the controller system being operatively coupled with the penile prosthesis structure through the inflating system, wherein operating the controller system governs transitioning of the penile prosthesis structure between an erect state and a flaccid state.

2. The automated penile prosthesis device of claim 1 further comprising:
the inflating system comprising a pneumatic hose, a pump, and a fluid reservoir;
the pneumatic hose being connected between the pump and the fluid reservoir;
the fluid reservoir being configured to hold a fluid;
the pneumatic hose being in fluid communication between the fluid reservoir, the pump, and the inflatable layer; and
the pump being operably coupled with the fluid reservoir, wherein actuating the pump transports the fluid between the fluid reservoir and the inflatable layer.

3. The automated penile prosthesis device of claim 2, wherein the inflatable layer is filled with the fluid during the erect state.

4. The automated penile prosthesis device of claim 2, wherein the inflatable layer is empty of the fluid during the flaccid state.

5. The automated penile prosthesis device of claim 1 further comprising:
the controller system comprising an electric and electronic system and a remote control device; and
the electric and electronic system being operatively coupled to the remote control device, wherein the remote control device is configured to remotely control functions of the electric and electronic system.

6. The automated penile prosthesis device of claim 5 further comprising:
the electric and electronic system comprising a microcontroller, a power source, at least one sensor, and a wireless communication module;
the inflating system comprising a pump;
the power source being electrically connected to the microcontroller, the pump, and the at least one sensor;
the wireless communication module being communicably connected to the remote control device; and
the microcontroller being electronically connected to the inflating system, the at least one sensor, and the wireless communication module.

7. The automated penile prosthesis device of claim 5, wherein the electric and electronic system being mounted adjacent to a terminal end of the penile prosthesis structure.

8. The automated penile prosthesis device of claim 5, wherein the remote-control device is detached from the penile prosthesis structure.

9. The automated penile prosthesis device of claim 5, wherein the inflating system is mounted adjacent to the electric and electronic system.

10. The automated penile prosthesis device of claim 1, wherein the semirigid core is made of silicone.

11. An automated penile prosthesis device comprising:
a penile prosthesis structure;
an inflating system; and
a controller system;
the penile prosthesis structure comprising a semirigid core, an inflatable layer, and a plurality of veins;
the inflating system comprising a pneumatic hose, a pump, and a fluid reservoir;
the inflating system being integrated between the controller system and the penile prosthesis structure;
the inflatable layer encapsulating the semirigid core;

the plurality of veins being integrated within the inflatable layer;

the plurality of veins being evenly distributed along a length of the inflatable layer;

the inflating system being configured to inflate the inflatable layer;

the pneumatic hose being connected between the pump and the fluid reservoir;

the fluid reservoir being configured to hold a fluid;

the pneumatic hose being in fluid communication between the fluid reservoir, the pump, and the plurality of veins;

the pump being operably coupled with the fluid reservoir, wherein actuating the pump transports the fluid between the fluid reservoir and the plurality of veins; and the controller system being operatively coupled with the penile prosthesis structure through the inflating system, wherein operating the controller system governs transitioning of the penile prosthesis structure between an erect state and a flaccid state.

12. The automated penile prosthesis device of claim 11, wherein the plurality of veins is filled with the fluid during the erect state.

13. The automated penile prosthesis device of claim 11, wherein the plurality of veins is empty of the fluid during the flaccid state.

14. The automated penile prosthesis device of claim 11 further comprising:

the controller system comprising an electric and electronic system and a remote control device; and the electric and electronic system being operatively coupled to the remote control device, wherein the remote control device is configured to remotely control functions of the electric and electronic system.

15. The automated penile prosthesis device of claim 14 further comprising:

the electric and electronic system comprising a microcontroller, a power source, at least one sensor, and a wireless communication module;

the power source being electrically connected to the microcontroller, the pump, and the at least one sensor;

the wireless communication module being communicably connected to the remote control device; and the microcontroller being electronically connected to the inflating system, the at least one sensor, and the wireless communication module.

16. The automated penile prosthesis device of claim 14, wherein the electric and electronic system being mounted adjacent to a terminal end of the penile prosthesis structure.

17. The automated penile prosthesis device of claim 14, wherein the remote-control device is detached from the penile prosthesis structure.

18. The automated penile prosthesis device of claim 11, wherein the semirigid core is made of silicone.

19. The automated penile prosthesis device of claim 11, wherein the pump is mounted adjacent to the electric and electronic system.

* * * * *